United States Patent [19]
Driesen et al.

[11] Patent Number: 5,652,990
[45] Date of Patent: Aug. 5, 1997

[54] BRUSH SECTION FOR AN ELECTRIC TOOTHBRUSH

[75] Inventors: Georges Driesen, Eschborn; Peter Hilfinger, Bad Homburg, both of Germany

[73] Assignee: Braun Aktiengesellschaft, Kronberg, Germany

[21] Appl. No.: 338,479

[22] PCT Filed: Mar. 8, 1994

[86] PCT No.: PCT/EP94/00705

§ 371 Date: Nov. 15, 1994

§ 102(e) Date: Nov. 15, 1994

[87] PCT Pub. No.: WO94/21192

PCT Pub. Date: Sep. 29, 1994

[30] Foreign Application Priority Data

Mar. 17, 1993 [DE] Germany .......................... 43 08 444.3

[51] Int. Cl.⁶ .................................................. A61C 17/22
[52] U.S. Cl. ..................... 15/28; 15/22.1; 15/180; 15/DIG. 5
[58] Field of Search ....................... 15/22.1, 28, 29, 15/167.1, 180, DIG. 5

[56] References Cited

U.S. PATENT DOCUMENTS

| | | | |
|---|---|---|---|
| 758,109 | 4/1904 | Sandiford | 15/167.1 |
| 1,896,731 | 2/1933 | Lippett | 15/28 |
| 1,947,324 | 2/1934 | Zerbee | 15/28 |
| 2,080,605 | 5/1937 | Duey | 15/167.1 |
| 2,140,307 | 12/1938 | Belaschk et al. | 15/28 |
| 2,155,245 | 4/1939 | Sekine | 15/167.1 |
| 2,558,332 | 6/1951 | Artale | 15/167.1 |
| 3,742,549 | 7/1973 | Scopp et al. | 15/167.1 |
| 4,020,522 | 5/1977 | Behrend | 15/28 |
| 4,619,009 | 10/1986 | Rosenstatter | 15/29 |
| 4,739,532 | 4/1988 | Behrend | 15/28 |
| 4,766,633 | 8/1988 | Clark | 15/167.1 |

FOREIGN PATENT DOCUMENTS

| | | | |
|---|---|---|---|
| 0 173 150 | 3/1986 | European Pat. Off. | |
| 2 587 183 | 3/1987 | France . | |
| 35 24 586 | 7/1985 | Germany . | |
| 3428860 | 2/1986 | Germany | 15/28 |
| 37 44 630 | 12/1987 | Germany . | |
| 4125168 | 4/1992 | Germany | 15/167.1 |
| 42 01 873 | 5/1993 | Germany . | |
| 91/07116 | 5/1991 | WIPO . | |
| 92-19125 | 11/1992 | WIPO | 15/167.1 |

*Primary Examiner*—Mark Spisich
*Attorney, Agent, or Firm*—Fish & Richardson, P.C.

[57] ABSTRACT

The invention is directed to a brush section for an electric toothbrush with a handle section comprising an electric motor, wherein the brush section is adapted to be connected with the handle section and has at its end remote from the handle section an essentially circular cylindrical rotary bristle supporting structure (38) on which bristles (48, 50) are arranged in the form of tufts (60, 62) of different lengths, and wherein the bristle supporting structure (38) has its axis of rotation at approximately right angles to a longitudinal center line of the brush section and is adapted to be driven in an alternating rotary motion over an arc of ±20° to ±100°. Some of the tufts (60) of bristles are serially located in position on a diameter and on an outer circular ring of the bristle supporting structure (38).

26 Claims, 3 Drawing Sheets

BRUSH SECTION FOR AN ELECTRIC TOOTHBRUSH

This invention relates to a brush section for an electric toothbrush with a handle section comprising an electric motor, wherein the brush section is adapted to be connected with the handle section and has at its end remote from the handle section an essentially circular cylindrical rotary bristle supporting structure on which bristles are arranged in the form of tufts, and wherein the bristle supporting structure has its axis of rotation at approximately right angles to a longitudinal center line of the brush section and is adapted to be driven in an alternating rotary motion, preferably over an arc of ±20° to ±100°.

From applicant's International Patent Application published under No. WO 91/07116, an electric toothbrush of this type is known in which the entire area of the bristle supporting structure is equipped with tufts of bristles of equal length.

Used in combination with the oscillatory drive mechanism, the brush has proven well in practice, producing excellent cleaning results even when used for relatively short periods only. Interproximal cleaning demands a relatively high degree of concentration from the user, making it necessary for the brush to be accurately aligned to the interproximal spaces using a slight tilting motion relative to the longitudinal center line.

It is an object of the present invention to improve upon a brush section for an electric toothbrush having a circular cylindrical bristle supporting structure in such a way as to provide an improved cleaning action of the interproximal spaces.

According to the present invention, this object is essentially accomplished in that the tufts of bristles are serially located in position on a diameter and on an outer circular ring of the bristle supporting structure. Arranging the tufts of bristles in this manner enables the bristles to enter the interproximal spaces readily and permits a thorough cleaning of this area, while the remaining bristles clean the tooth surfaces as usual. The helical motion performed by the longer bristles as a result of the alternating rotary motion of the bristle supporting structure, in which the center (axis of rotation) of the bristles fixedly secured on the diameter is not moved, supports the penetrating action of the bristles into the interproximal space, in addition to making it easy for the user to centrally locate the brush within the interproximal space. Owing to the oscillatory cleaning motion, the bristles conform themselves to the different contours of the interproximal spaces, whereby overall a very good cleaning function can be accomplished.

Particularly suitably, the bristles of those tufts that are not fixedly secured on the diameter or on the outer circular ring of the bristle supporting structure differ in the direction of smaller values from the bristles of the tufts arranged on the diameter or on the outer circular ring at least in one of the following magnitudes: length, diameter or number. It is thereby achieved that the bristles in the inner field behave differently from the bristles on the diameter or on the outer circular ring.

For example, if the bristles in the inner field are shorter than the bristles on the diameter and on the outer circular ring, the bristles in the inner field will be engaged against the tooth surfaces, cleaning them in the process, whilst the longer bristles on the diameter will serve the function of cleaning the interproximal spaces, and the equally longer bristles on the outer circular ring will remove plaque in the tooth-gingiva junction region.

In a further configuration of the present invention, the bristles in the inner field are of a diameter smaller than that of the bristles on the diameter or on the outer circular ring, while being of equal or different length. The rigidity of the longer bristles on the diameter and on the outer circular ring is increased as a result of the larger bristle diameter, so that these more rigid bristles are again particularly advantageously suitable for cleaning the interproximal spaces and the tooth-gingiva junction region.

In a further embodiment, it has proven to be very advantageous to provide in the inner field only very few or no tufts of bristles at all. In this arrangement, the bristles of the tufts in the inner field may also be shorter and/or thinner than the remaining bristles. The low number of bristles in the inner field as compared with the number of bristles on the diameter and on the outer circular ring has the effect that the few bristles in the inner field, while they do clean the tooth surfaces, are not in a position to bear so heavily against the tooth surfaces as to enable the bristles of the tufts on the diameter and on the outer circular ring to enter the interproximal space for cleaning.

In all these modification possibilities afforded by the present invention, the added possibility exists to provide the bristles of the tufts fixedly secured on the diameter with a length and/or a diameter that differs from that of the bristles of the tufts fixedly secured on the outer circular ring.

In another advantageous configuration of the present invention, no further bristles are provided on the bristle supporting structure except for the bristles of those tufts that are fixedly secured on the diameter and on the outer circular ring. Accordingly, no bristles are provided in the inner field referred to in the foregoing. On the one hand, these bristles penetrate the interproximal spaces particularly deeply and clean the tooth-gingiva junction regions. On the other hand, the bristles on the diameter and on the outer circular ring equally serve the function of cleaning the tooth surfaces as they are moved across them. The result is a complete cleaning action of the tooth surfaces concomitant with an improved cleaning function of the interproximal spaces and the tooth-gingiva junction region.

This configuration also provides the added possibility of varying the length and/or the diameter of the bristles on the diameter and of the bristles on the outer circular ring. In particular, it may be suitable to provide the bristles on the diameter with a length greater than that of the bristles on the outer circular ring. In this manner, further advantageous cleaning actions may be accomplished as has already been set forth in a different context.

In an advantageous further feature of the present invention, the tufts of bristles fixedly secured in place on the outer circular ring of the bristle supporting structure are of a length greater than that of the tufts of bristles fixedly secured in place on the diameter. In this manner, cleaning of the tooth-gingiva junction region can be particularly enhanced. This further feature is particularly suitable in cases where no inner field is provided. However, it is also possible to combine the further feature identified with any other configuration and further feature so far described.

Because the tufts of bristles fixedly secured on the diameter are at approximately right angles to the longitudinal center line of the brush section when the brush supporting structure is in a central or normal position, the serially arranged longer bristles are readily and reliably aligned to the interproximal space to be cleaned when the electric toothbrush is in a normal orientation relative to the teeth, simplifying manipulation by the user significantly.

Advantageously, the tufts having the shorter bristles are arranged on the bristle supporting structure on two approximately concentric circular rings. This results in a favorable distribution of the tufts on the bristle supporting structure, making effective use of the area of the bristle supporting structure available for carrying the bristles.

Because the longer bristles protrude beyond the shorter bristles by 1.5 mm, approximately, the longer bristles are in a position to enter and thus effectively clean the interproximal space readily, while the shorter bristles remove plaque from the tooth surfaces with ease.

In an advantageous embodiment, the shorter bristles have a diameter of 5 to 6 mils (1 mil=0.0254 mm), and the longer bristles have a diameter greater than 6 to 7 mils. By varying the bristle diameters in combination with the different bristle lengths, all bristles are of about the same rigidity overall.

Moreover, the tufts comprising the longer bristles are advantageously color-coded, enabling the user of such a brush with its improved cleaning properties to see from a change in color that a brush replacement is required or recommended.

In an advantageous configuration of the present invention, the angle of rotation of the bristle supporting structure is preferably about ±35° related to the central or normal position of the bristle supporting structure. This indicates an area in which a particularly effective cleaning function of the interproximal spaces is performed.

The following brush section configurations have proven to be particularly advantageous. The outer circular ring is equipped with 12±2 tufts of bristles, approximately, with the bristles having a length of between 8 and 9 (±1) mm, approximately, and a diameter of 6±1 mils.

About 6±1 tufts of bristles are provided on the diameter, the bristles having a length of between 8 and 9 (±1) mm, approximately, and a diameter of 6±1 mils, approximately. The inner field, unless entirely devoid of bristles, is equipped with 2 to 6±2 tufts, approximately, the associated bristles having a length of between 7 and 9 (±1) mm, approximately, and a diameter of between 5 and 6 (±1) mils, approximately.

Further objects, features, advantages and application possibilities of the present invention will become apparent from the subsequent description of embodiments. It will be understood that all features described and/or represented by illustration, whether taken alone or in any desired combination, constitute the subject-matter of the present invention, irrespective of their summarization in the claims or their back-references.

Figure 1:
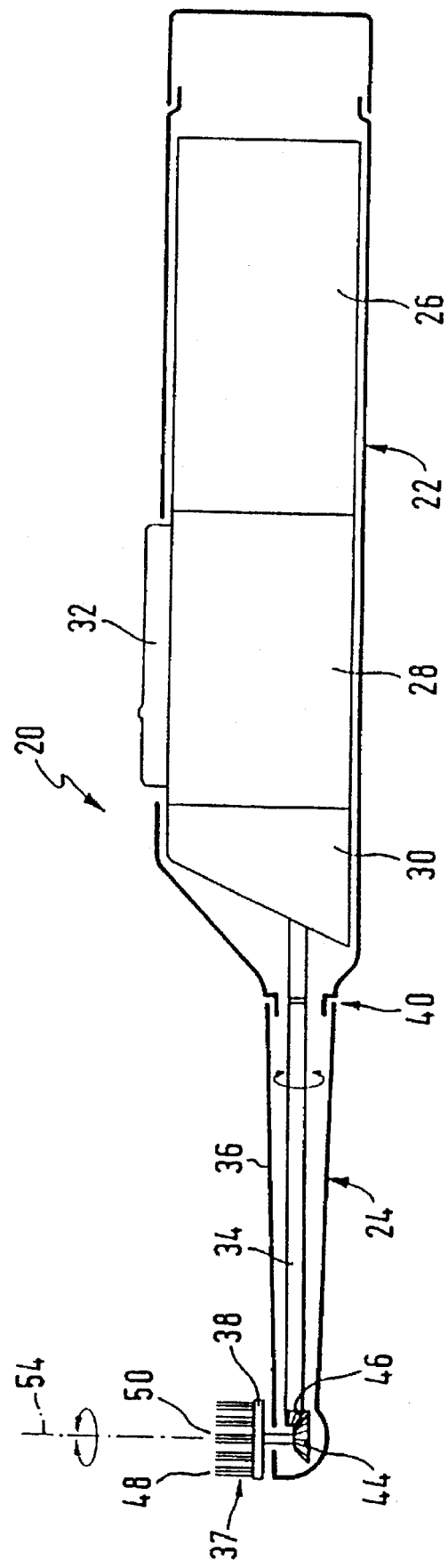
FIG. 1 is a schematic side view of an electric toothbrush.

Referring now to FIG. 1 of the drawings, reference numeral 20 identifies an electric toothbrush. The toothbrush 20 comprises a handle section 22 and a brush section 24 adapted to be coupled thereto. The handle section 22 houses an accumulator 26 or, alternatively, a battery, an electric motor 28, as well as a drive system 30 for transforming the continuous rotary motion of the electric motor into an oscillatory motion. On the outside of the handle section 22 is a switch 32 for activating the toothbrush 20. The brush section 24 comprises a hollow mounting tube 36 receiving a shaft 34. The mounting tube 36 and the shaft 34 are adapted to be connected to the handle section 22 by a coupling means 40 not shown in greater detail. Arranged at the end of the brush section 24 remote from the handle section 22 is a bristle supporting structure 38 for receiving bristles 48, 50 or tufts 60, 62, 64, 66 of bristles. The brush 37 is caused to oscillate by a bevel gear 44 at the end of the bristle supporting structure 38 and a mating bevel gear segment 46 at the head end of the shaft 34. The range of the angle of rotation covered by the bristle supporting structure 38 preferably assumes values on the order of ±35°±5°, approximately, with values in the range of between ±20° and ±100° being, however, also possible. The axis of rotation 54 of the bristle supporting structure 38 defines an angle of about 90° with respect to the axis of rotation of the shaft 34. The toothbrush of FIG. 1 is described in detail in applicant's International Patent Application published under No. WO 91/07116 which is included in the disclosure content of the present application by express reference thereto.

Figure 2:
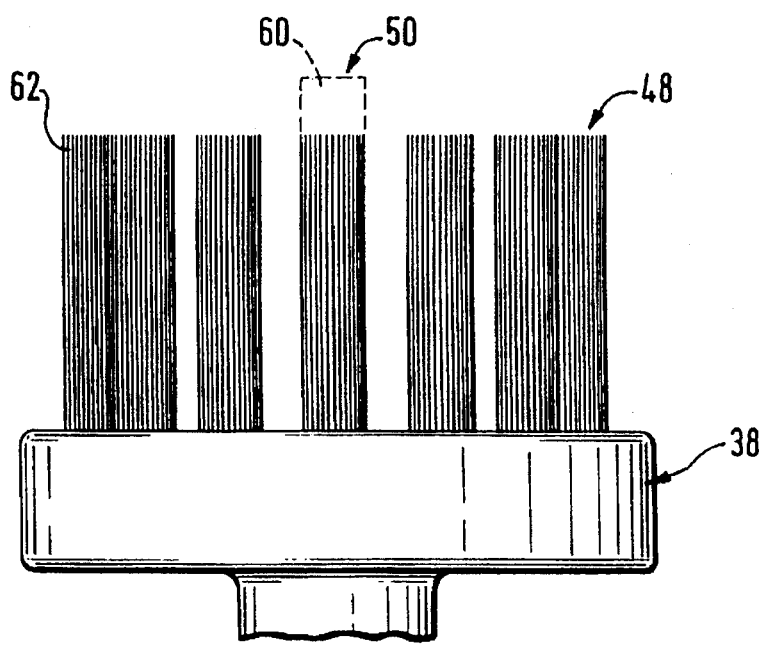
FIG. 2 is a view of a bristle supporting structure with bristles, illustrating a first embodiment.

In FIG. 2, a bristle supporting structure 38 according to a first embodiment is equipped with tufts 62 of bristles 48 of shorter length, the arrangement being interrupted by a row of tufts 60 of longer bristles 50 disposed approximately centrally on the bristle supporting structure 38. To illustrate this arrangement more clearly, the space existing between the shorter bristles 48 and the longer bristles 50 is shown on a slightly enlarged scale.

Figure 3:
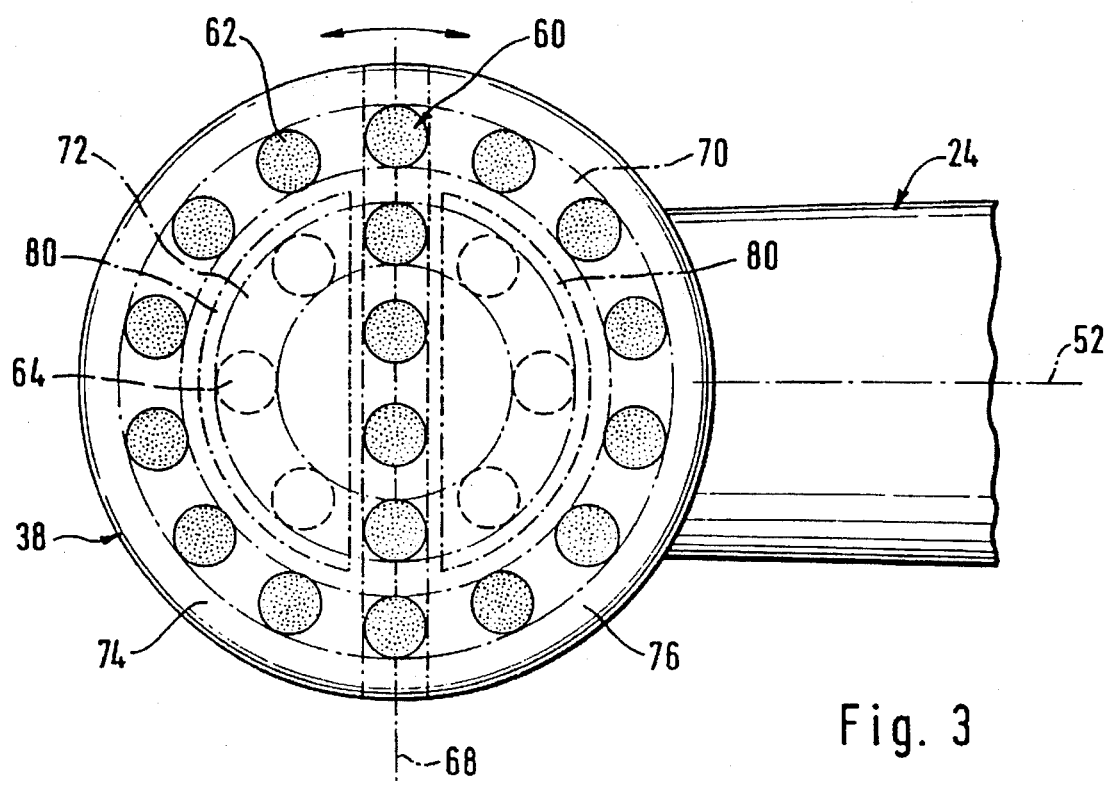
FIG. 3 is a top plan view of a brush section (partial representation) showing the bristle supporting structure and the bristles of FIG. 2.

The arrangement of the shorter bristles 48 and the longer bristles 50 on the bristle supporting structure 38 is illustrated in FIG. 3. The tufts 60 with the longer bristles 50 are fixedly secured in place on a diameter 68 of the bristle supporting structure 38. In the central position of the bristle supporting structure 38 shown, the tufts 60 fixedly held on the diameter 68 are at approximately right angles to a longitudinal center line 52 of the brush section 24. In this normal/central position of the bristle supporting structure 38, the tufts 60 having the longer bristles 50 can be advantageously aligned to the interproximal space without the need to move the electric toothbrush 20 from its normal cleaning position. By virtue of the oscillatory motion of the bristle supporting structure 38 over an arc of ±20° to ±100°, preferably ±35°, related to the normal position, the longer bristles 50 enter the interproximal spaces to perform a cleaning function. The tufts 62, 64 having the shorter bristles 48 are arranged to the right and left of the diameter 68 on two circular segments 74, 76 and/or on two approximately concentric circular rings 70, 72. As a result of the oscillatory motion of the bristle supporting structure 38 during the cleaning action, the teeth as well as the adjoining area of the tooth-gingiva junction region are cleaned by the shorter bristles 48, while at the same time the longer bristles 50 perform a thorough cleaning function within the interproximal spaces without the shorter bristles 48 and the longer bristles 50 obstructing each other in any manner. The user maneuvers the electric toothbrush in the conventional fashion.

In a second embodiment, the bristle supporting structure 38 carries tufts 60, 66 comprised of longer bristles 50 both on the diameter 68 and on the outer circular ring 70, these areas overlapping each other partially in the region 78. In the central position of the bristle supporting structure 38, the tufts 60 fixedly located on the diameter 68 are at approximately right angles to the longitudinal center line 52 of the brush section 24. When the bristle supporting structure 38 is driven in an oscillatory fashion, the longer bristles 50 located on the diameter 68 will enter the interproximal spaces, whilst the longer bristles 50 on the outer circular ring 70 will clean particularly the tooth-gingiva junction region. The shorter bristles 48 of the tufts 64 will bear against the tooth surfaces, cleaning them. This combined action of longer bristles 50 on the diameter 68 and on the outer circular ring 70 of the bristle supporting structure 38, with the shorter bristles 48 arranged in-between, thus effects a thorough cleaning of the interproximal spaces, the tooth outer and inner surfaces, as well as the tooth-gingiva junction region.

Figure 5:
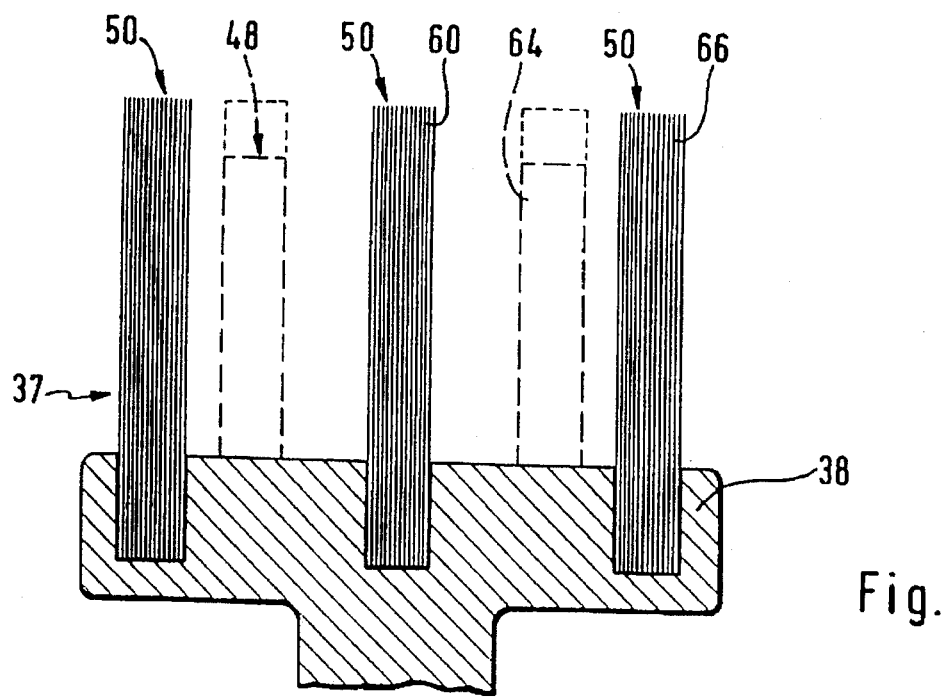
FIG. 5 is a longitudinal sectional view of the bristle supporting structure with bristles, taken along the line 5—5 of FIG. 4.
Figure 4:
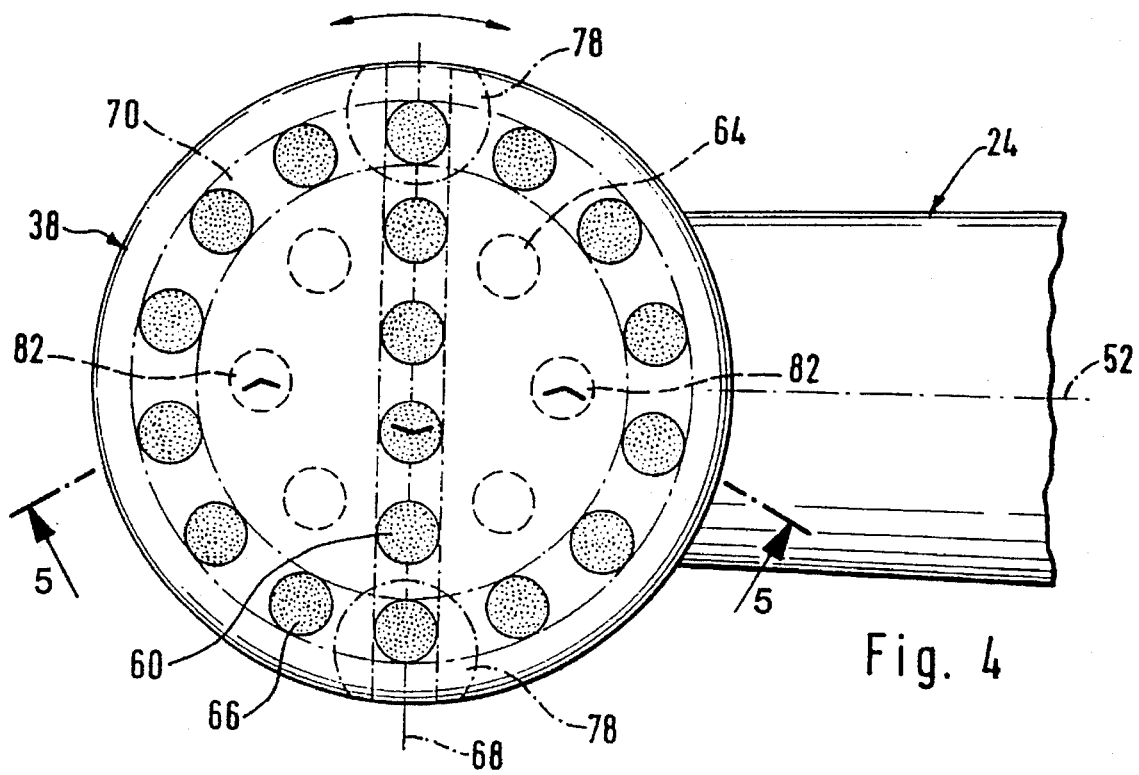
FIG. 4 is a top plan view of a bristle supporting structure with bristles and brush section, illustrating a second embodiment.

FIG. 5 illustrates clearly the arrangement of the tufts 60, 64, 66 of different lengths of bristles 48, 50 in the bristle supporting structure 38. The diameter of the longer bristles 50 which is preferably between 6 and 7 mils is greater than that of the shorter bristles 48 which is in the range of between 5 and 6 mils. The enhanced rigidity of the bristles 50 resulting from the larger diameter may be considered balanced out by the greater length of the bristles 50 so that shorter and longer bristles 48, 50 are of approximately equal rigidity, resulting in a brush 37 which may be classified as soft. Particularly advantageously, the tufts 60, 66 with the longer bristles 50 are color-coded, the bristles changing their color in use to provide a visual indication to the user that the brush 37 is in need of replacement.

In a further embodiment, the bristles of the tufts 62 fixedly secured on the outer circular ring 70 of the bristle supporting structure 38 are of a length greater than that of the bristles of the tufts 60 fixedly secured on the diameter 68. In all other respects, the arrangement of the individual tufts 60, 62, 64 is the same as in FIG. 3.

In each of the three embodiments described, an inner field 80 comprised of two approximately semi-circular segments is provided, the field being formed by tufts 64 fixedly secured on the inner circular ring 72. The length of the bristles of the tufts 64 in the inner field may be equal to or smaller than the length of the bristles of the tufts 62, 60 on the outer circular ring 70 and on the diameter 68, respectively. In further modifications, the added or alternative possibility exists to make the diameter of the bristles of the tufts 64 in the inner field 80 equal to or smaller than the diameter of the bristles of the tufts 62, 60 on the outer circular ring 70 and on the diameter 68, respectively.

Again as an addition or alternative to the previous modifications, it is further possible that the number of bristles, that is, in particular the number of the individual bristle filaments or of the tufts 64 of the inner area is essentially smaller than the number of bristles or tufts 62, 60 on the outer circular ring 70 and on the diameter 68, respectively. In particular one embodiment provides only one tuft 64 each on the inner circular ring 72 on either side of the diameter 68.

In further embodiments, no bristled inner field 80 is provided in contrast to the three embodiments identified and described in the foregoing. This means that no tufts 64 are provided on the inner circular ring 72. Thus, only the tufts 60 on the diameter 68 and the tufts 62 on the outer circular ring 70 are provided. As in the three embodiments previously described, the length of the tufts 60 on the diameter 68 may be greater than, equal to, or smaller than, the length of the tufts 62 on the outer circular ring 70. In a further feature of this embodiment, two tufts 82, one in each segment, are provided in the inner field 80.

In the embodiments having no inner field it is further possible that the bristles of the tufts 62 on the outer circular ring 70 and the bristles of the tufts 60 on the diameter 68, whether alternatively or in combination, are of equal or different lengths or of equal or different bristle diameters.

We claim:

1. A brush section for an electric toothbrush with a handle section having an electric motor, wherein the brush section comprises a first end adapted to be connected with the handle section, a second end remote from the handle section, and an essentially circular cylindrical rotary bristle supporting structure on the second end, the bristle supporting structure including an end surface on which bristles are arranged in the form of tufts, wherein the bristle supporting structure has an axis of rotation at an approximately right angle to a longitudinal center line of the brush section and is adapted to be driven by a coupling to the electric motor in an alternating rotary motion, wherein a first group of the tufts of bristles are serially located in position on a diameter, and a second group of the tufts are arranged on an outer circular ring of the bristle supporting structure, wherein the first group of tufts of bristles serially located on the diameter includes four tufts located inside the outer circular ring.

2. A brush section as claimed in claim 1, wherein an inner field of the bristle supporting structure between the tufts located on the diameter and outer circular ring of the bristle supporting structure is devoid of bristles.

3. A brush section as claimed in claim 1, further comprising tufts of bristles arranged on an inner circular ring between the tufts located on the diameter and the outer circular ring of the bristle supporting structure.

4. A brush section as claimed in claim 3, wherein the tufts arranged on the inner circular ring comprise bristles of a diameter smaller than the diameter of the bristles of the tufts located on the diameter and the outer circular ring of the bristle supporting structure.

5. A brush section as claimed in claim 3 wherein the tufts arranged on the inner circular ring comprise bristles of a length shorter than the length of the bristles of the tufts located on the diameter and the outer circular ring of the bristle supporting structure.

6. A brush section as claimed in claim 3 wherein the number of bristles of the tufts arranged on the inner circular ring is smaller than the number of bristles of the tufts located on the diameter and the outer circular ring of the bristle supporting structure.

7. A brush section as claimed in claims 1 or 3 wherein the bristles of the tufts arranged on the outer circular ring differ in one of the group of characteristics consisting of length, diameter and number per tuft from the bristles of the tufts arranged on the diameter of the bristle supporting structure.

8. A brush section as claimed in claim 1 wherein a single tuft of bristles is arranged approximately centrally in an inner field of the bristle supporting structure between the tufts located on the diameter and the outer circular ring of the bristle supporting structure.

9. A brush section as claimed in claim 1 wherein the bristles of the tufts located on the diameter and on the outer circular ring of the bristle supporting structure are of equal length.

10. A brush section as claimed in claim 1 wherein the tufts of bristles on the diameter of the bristle supporting structure are at approximately a right angle to the longitudinal center line of the brush section when the bristle supporting structure is in a central position.

11. A brush section as claimed in claim 1 wherein the bristles of the tufts arranged on the diameter of the bristle supporting structure are of a length greater than that of the bristles of the other tufts.

12. A brush section as claimed in claim 11, wherein the tufts having the shorter bristles are arranged on the bristle supporting structure on two approximately concentric circular rings.

13. A brush section as claimed in claim 7 wherein the bristles of the tufts arranged on the outer circular ring differ in length from the bristles of the tufts arranged on the diameter of the bristle supporting structure, and wherein the tufts having the longer bristles protrude beyond the tufts having the shorter bristles by approximately 1.5 mm.

14. A brush section as claimed in claim 7 wherein the bristles of the tufts arranged on the outer circular ring differ in length from the bristles of the tufts arranged on the diameter of the bristle supporting structure, and wherein the tufts having the shorter bristles have a diameter of 5 to 6 mils, and the tufts having the longer bristles have a diameter of 6 to 7 mils.

15. A brush section as claimed in claim 7 wherein the bristles of the tufts arranged on the outer circular ring differ in length from the bristles of the tufts arranged on the diameter of the bristle supporting structure, and wherein the tufts comprising the longer bristles are color-coded.

16. A brush section as claimed in claim 1 wherein the angle of rotation of the bristle supporting structure is about ±20° to ±100°, related to a normal position of the bristle supporting structure.

17. A brush section as claimed in claim 1 wherein the outer circular ring is equipped with 12 tufts, approximately, the bristles having a length of between approximately 8 and 9 mm, approximately, and a diameter of approximately 6 mils, approximately.

18. A brush section as claimed in claim 1 wherein the first group of tufts includes six tufts, approximately, arranged on the diameter, the bristles having a length of between 8 and 9 mm, approximately, and a diameter of 6 mils, approximately.

19. A brush section as claimed in claim 1 wherein an inner field positioned between the first group of tufts located on a diameter and the second group of tufts arranged on an outer circular ring is equipped with two to six tufts, approximately, the bristles having a length of between 7 and 9 mm, approximately, and a diameter of between 5 and 6 mils, approximately.

20. An electric toothbrush, comprising:
a handle section, including an electric motor;
a brush section having a longitudinal center line, and including a first end adapted to be connected with the handle section and a second end remote from the handle section;
the second end of the brush section including an essentially circular cylindrical rotary bristle supporting structure on an end surface of which bristles are arranged in the form of tufts, wherein the bristle supporting structure has an axis of rotation at an approximately right angle to the longitudinal center line and is adapted to be driven in an alternating rotary motion by a coupling to the electric motor when the brush section is connected to the handle section, wherein approximately six tufts of bristles are serially located in position on a diameter of the bristle supporting structure, tufts of bristles are arranged on an outer circular ring of the bristle supporting structure, and approximately six tufts of bristles are located in an inner circular area between the tufts on the diameter and the tufts on the outer circular ring.

21. A brush section for an electric toothbrush with a handle section including an electric motor, wherein the brush section comprises:
a first end adapted to be connected with the handle section;
a second end remote from the handle section, the second end including an essentially circular cylindrical rotary bristle supporting structure on an end surface of which bristles are arranged in the form of tufts, and wherein the bristle supporting structure has an axis of rotation at an approximately right angle to a longitudinal center line of the brush section and is adapted to be driven by a coupling to the electric motor in an alternating rotary motion;
wherein a first group of the tufts are serially located on a diameter of the bristle supporting structure;
wherein a second group of the tufts are arranged on an outer circular ring of the bristle supporting structure; and
wherein a third group of tufts are positioned within the outer circular ring between the first group of tufts and the second group of tufts, the bristles of the third group of tufts having a smaller diameter than the diameter of at least one of the bristles of the first group of tufts and the bristles of the second group of tufts.

22. The brush section of claim 21, wherein the bristles within the outer circular ring are shorter than the bristles on the outer circular ring.

23. A brush section comprising:
a first end adapted to be connected to a handle section of an electric toothbrush that includes a motor, and
an essentially circular cylindrical rotary bristle supporting structure disposed on an end portion of the brush section remote from the first end adapted to be connected to the handle section, having an axis of rotation at an approximately right angle to a longitudinal axis of the handle section and adapted to be driven in an alternating rotary motion by a coupling to the motor when the brush section is connected to the handle section, the bristle supporting structure including a surface on which bristles are arranged in the form of tufts serially located along a diameter of the bristle supporting structure, tufts located on an outer circular ring of the bristle supporting structure, and tufts arranged on an inner circular ring of the bristle supporting structure between the tufts along the diameter and the tufts arranged on the outer circular ring, wherein the bristles of the tufts, located respectively on the diameter and outer circular ring of the bristle supporting structure, are longer than and have a larger diameter than bristles of the tufts arranged on the inner circular ring.

24. A brush section as claimed in claim 23, wherein the diameter of the bristles of the tufts arranged on the diameter and outer circular ring of the bristle supporting structure is approximately 6 mil and the diameter of the bristles of the tufts arranged on the inner circular ring is approximately 5 mil.

25. A brush section as claimed in claim 24, wherein the number of bristles of the tufts arranged on the inner circular ring is smaller than a combination of the number of bristles of the tufts located on the diameter and the outer circular ring of the bristle supporting structure.

26. A brush section comprising:
a first end adapted to be connected to a handle section of an electric toothbrush that includes a motor, and
an essentially circular cylindrical rotary bristle supporting structure disposed on an end portion of the brush section remote from the first end adapted to be connected to the handle section, having an axis of rotation at an approximately right angle to a longitudinal axis of the handle section and adapted to be driven in an alternating rotary motion by a coupling to the motor when the brush section is connected to the handle section, the bristle supporting structure including a surface on which bristles are arranged in the form of tufts serially located along a diameter of the bristle supporting structure, tufts located on an outer circular ring of the bristle supporting structure, and tufts arranged on an inner circular ring of the bristle supporting structure between the tufts along the diameter and the tufts arranged on the outer circular ring, wherein the bristles of the tufts, located respectively on the diameter and outer circular ring of the bristle supporting structure, are longer than bristles of the tufts arranged on the inner circular ring, wherein the outer circular ring is equipped with approximately 12 tufts, the diameter of the bristle supporting structure with approximately six tufts and the inner circular ring with approximately six tufts.

* * * * *